United States Patent
Conley et al.

(10) Patent No.: US 10,307,232 B2
(45) Date of Patent: Jun. 4, 2019

(54) PACKAGED ORTHODONTIC ASSEMBLY WITH ANGLED SUPPORT STRUCTURE

(71) Applicant: 3M INNOVATIVE PROPERTIES COMPANY, St. Paul, MN (US)

(72) Inventors: Alan F. Conley, LaVerne (CA); John A. Verdouw, Ontario (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/554,359

(22) PCT Filed: Mar. 7, 2016

(86) PCT No.: PCT/US2016/021231
§ 371 (c)(1),
(2) Date: Aug. 29, 2017

(87) PCT Pub. No.: WO2016/144896
PCT Pub. Date: Sep. 15, 2016

(65) Prior Publication Data
US 2018/0177577 A1    Jun. 28, 2018

Related U.S. Application Data

(60) Provisional application No. 62/131,003, filed on Mar. 10, 2015.

(51) Int. Cl.
*A61C 19/02* (2006.01)
*A61C 7/14* (2006.01)
(Continued)

(52) U.S. Cl.
CPC ............. *A61C 19/02* (2013.01); *A61C 7/12* (2013.01); *A61C 7/14* (2013.01); *A61C 7/282* (2013.01);
(Continued)

(58) Field of Classification Search
CPC ....... A61C 19/02; A61C 7/16; A61C 2202/00; B65D 81/022; B65D 25/106
(Continued)

(56) References Cited

U.S. PATENT DOCUMENTS

| 1,992,950 A | 3/1935 | Horner |
| 3,529,716 A | 9/1970 | O'Connell |

(Continued)

FOREIGN PATENT DOCUMENTS

| JP | H08-140994 | 6/1996 |
| WO | WO 1993-002630 | 2/1993 |

(Continued)

OTHER PUBLICATIONS

International Search Report for PCT International Application No. PCT/US2016/021231, dated May 10, 2016, 4 pages.
(Continued)

*Primary Examiner* — Steven A. Reynolds

(57) ABSTRACT

Packaged orthodontic assemblies include a chamber, an orthodontic appliance, and a support structure engaged with the appliance to secure the appliance in the chamber. The support structure can include a post complemental to a partially enclosed passage, typically an arch wire slot, in the appliance body. The support may orient the wall sections of the enclosed passage at an acute angle relative to a chamber side wall.

16 Claims, 7 Drawing Sheets

(51) Int. Cl.
*A61C 7/28* (2006.01)
*B65D 25/10* (2006.01)
*A61C 7/12* (2006.01)

(52) U.S. Cl.
CPC ........ *B65D 25/106* (2013.01); *A61C 2202/00* (2013.01); *A61C 2202/01* (2013.01)

(58) Field of Classification Search
USPC .................................... 206/63.5, 438, 368
See application file for complete search history.

(56) References Cited

U.S. PATENT DOCUMENTS

| | | | |
|---|---|---|---|
| 4,978,007 A | 12/1990 | Jacobs | |
| 5,015,180 A | 5/1991 | Randklev | |
| 5,328,363 A * | 7/1994 | Chester | A61C 7/12 206/63.5 |
| 5,354,199 A | 10/1994 | Jacobs | |
| 5,538,129 A * | 7/1996 | Chester | A61C 19/02 206/469 |
| 5,575,645 A | 11/1996 | Jacobs | |
| 5,810,582 A | 9/1998 | Doyle | |
| 5,827,058 A | 10/1998 | Kelly | |
| 6,089,861 A | 7/2000 | Kelly | |
| 6,183,249 B1 | 2/2001 | Brennan | |
| 6,834,761 B1 | 12/2004 | Kesling | |
| 6,960,079 B2 | 11/2005 | Brennan | |
| 7,726,470 B2 | 6/2010 | Cinader, Jr. | |
| 7,841,464 B2 | 11/2010 | Cinader, Jr. | |
| 7,910,632 B2 | 3/2011 | Cinader, Jr. | |
| 8,925,719 B2 * | 1/2015 | Kesling | A61C 19/02 206/369 |
| 2003/0196914 A1 | 10/2003 | Tzou | |
| 2005/0133384 A1 | 6/2005 | Cinader | |
| 2005/0241962 A1 * | 11/2005 | Tuneberg | A61C 7/00 206/63.5 |
| 2006/0207893 A1 | 9/2006 | Cinader | |
| 2008/0044787 A1 | 2/2008 | Cinader, Jr. | |
| 2008/0096150 A1 | 4/2008 | Cinader | |
| 2008/0286710 A1 | 11/2008 | Cinader, Jr. | |
| 2009/0233252 A1 | 9/2009 | Cinader, Jr. | |
| 2011/0171591 A1 | 7/2011 | Amos | |
| 2011/0247947 A1 * | 10/2011 | Nihei | A61C 8/0087 206/63.5 |
| 2015/0021210 A1 | 1/2015 | Kesling | |

FOREIGN PATENT DOCUMENTS

| | | |
|---|---|---|
| WO | WO 1999-017674 | 4/1999 |
| WO | WO 2005-065567 | 7/2005 |
| WO | WO 2007-149710 | 12/2007 |
| WO | 2008/066597 | 6/2008 |
| WO | WO 2008-144123 | 11/2008 |
| WO | WO 2010-039395 | 4/2010 |
| WO | WO 2013-162975 | 10/2013 |

OTHER PUBLICATIONS

Extended European Search Report for European Patent Application No. 16762310.7, dated Sep. 24, 2018.

* cited by examiner

PACKAGED ORTHODONTIC ASSEMBLY WITH ANGLED SUPPORT STRUCTURE

BACKGROUND

Orthodontics is a specialized area of dentistry concerned with the diagnosis and treatment of dental malocclusions to improve bite function, hygiene, and facial aesthetics. Orthodontic therapy commonly uses appliances called brackets and molar tubes which are bonded to a patient's teeth. Brackets and molar tubes contain slots and passageways, respectively, to accommodate a resilient "U"-shaped wire called an orthodontic archwire. During treatment, the archwire is secured within the slots and passageways of the brackets and molar tubes. While the archwire is initially distorted, it gradually returns to its original shape over the course of treatment, thereby applying therapeutic forces to urge the malpositioned teeth to proper locations.

Brackets, molar tubes, and other bondable appliances are generally affixed to teeth using a suitable orthodontic adhesive. Traditionally, adhesives were painstakingly applied, one at a time, to each appliance by an orthodontic assistant at the orthodontic office. Since this can be a tedious process, manufacturers have provided appliances that are coated in advance, or "pre-coated," at the factory to save time for the orthodontist. Coated appliance configurations are described in detail in issued U.S. Pat. No. 4,978,007 (Jacobs, et al.), U.S. Pat. No. 5,015,180 (Randklev), and U.S. Pat. No. 5,328,363 (Chester et al.).

Pre-coated brackets and molar tubes provide a significant advantage to the practitioner. First, these appliances provide for a high degree of precision in the amount of adhesive that is dispensed on the base of each appliance compared with hand-coating appliances. Second, these appliances are easy to use and save time, since a practitioner can conveniently remove a bracket from its respective container and place it directly on the patient's tooth without need for intervening steps. Typically, the adhesive is a light curable adhesive which allows the appliance, once placed on the tooth surface, to be carefully positioned in a proper orientation before a curing lamp is activated to cure the adhesive and securely fix the appliance in place.

Various approaches have been taken in packaging adhesive-coated orthodontic appliances. In one approach, the appliance and adhesive are placed in a sealed "blister" or similar disposable container. The adhesive is secured against a wall of the container having a suitable release surface such that the appliance and adhesive lift off together when the appliance is plucked from the container. This approach is described in, for example, issued U.S. Pat. No. 6,183,249 (Brennan, et al.). Another approach involves using mechanical structures to suspend the appliance in the container such that the adhesive does not contact any surfaces of the container. Examples of this approach are described in issued U.S. Pat. No. 5,827,058 (Kelly, et al.) and U.S. Pat. No. 6,089,861 (Kelly, et al.), as well as International Publication WO/2013/162975 (Conley, et al.).

SUMMARY OF THE INVENTION

In packaging an adhesive-coated orthodontic appliance, it can be challenging to provide ease of use in dispensing the appliance from the package while also ensuring that the appliance is properly secured during transportation and handling. Using some conventional packaging methods described in U.S. Pat. No. 6,183,249 (Brennan, et al.) for example, the adhesive on the appliance is often in contact with a portion of the package, which can result in adhesive residue left behind when the appliance is removed from the package or displaced relative to its desired position. This reduces the usable amount of adhesive on the appliance, which can be problematic for proper bonding of the appliance to a patient's tooth. While this contact can be alleviated by suspending the appliance within the container, the lack of contact with bottom of the container presents its own unique challenges. One of the difficulties of suspending an orthodontic appliance with a single package design is the range of appliance geometries. Such variation may be due to differences in appliance prescription (e.g., torque and angulation), design, base size, minor defects, or even manufacturing tolerances.

Advantageously, the assemblies and methods of the present disclosure enable the appliance to be held securely during shipping and handling by engaging an arch wire slot or other partially enclosed passage of the appliance. This protects the appliance and also preserves the integrity of an adhesive pad on the base of the appliance. Moreover, because the support is conveniently withdrawn from the appliance as the user lifts the appliance from the package, there can be an abundance of space along the periphery of the appliance to provide easy access using tweezers or other hand instruments. Finally, by bracing the appliance within the container, these assemblies alleviate the burden on the adhesive to support the appliance during transit, leading to greater freedom in engineering the composition of the adhesive and the dimensions of the container.

In one aspect, the present disclosure provides a packaged orthodontic assembly comprising a container with a chamber, the chamber including a sidewall and a bottom wall and the bottom wall defining a reference plane. An orthodontic appliance is received in the chamber, the appliance including a base and a passage having a lingual wall. A support extends into the chamber and is engaged with the orthodontic appliance and orients the appliance such that the lingual wall is not parallel to the reference plane.

In another aspect, the present disclosure provides a packaged orthodontic assembly comprising a container with a chamber, the chamber including a sidewall and a bottom wall. An orthodontic appliance is received in the chamber, the appliance including a base and a partially enclosed passage. A support extends into the chamber and includes a post having a length, at least a portion of the post's length is received in the passage, securing the appliance in the container.

In yet another aspect, the present disclosure provides a packaged orthodontic assembly comprising. A container with a chamber, the chamber including a sidewall and a bottom wall. An orthodontic appliance is received in the chamber, the appliance including a base and a partially enclosed passage, with the base including a hardenable dental composition extending across at least a portion of the base. A support is removably received in the chamber and includes a post having a length. A portion of the post's length is received in the passage, securing the appliance in the chamber.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Directional Definitions

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF ILLUSTRATIVE EMBODIMENTS

Figure 1:
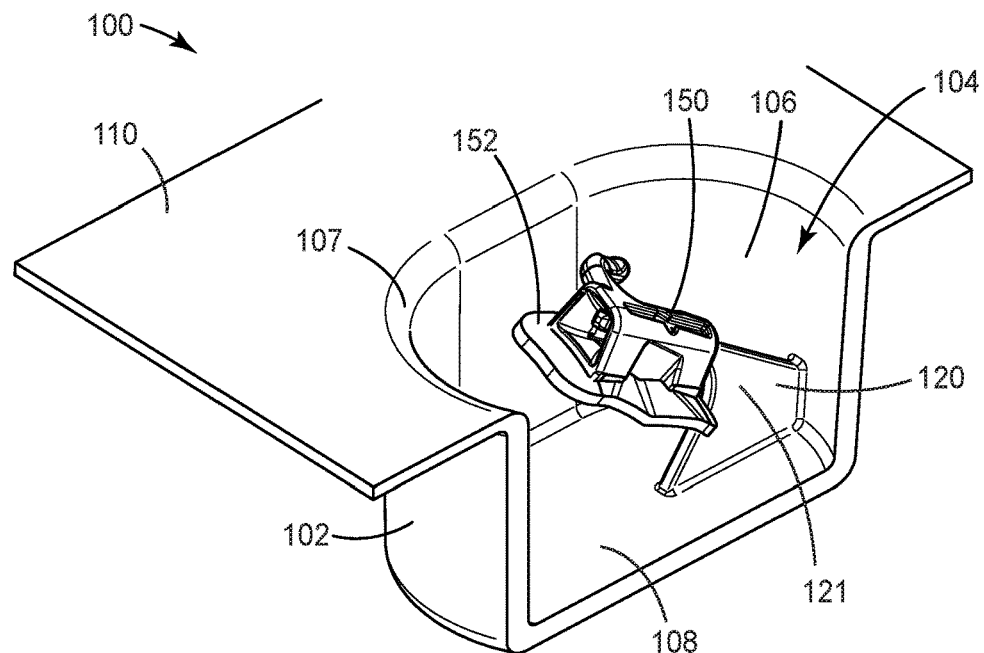
FIG. 1 is a cut-away, isometric view of a packaged orthodontic assembly according to one embodiment of the present disclosure.

According to one exemplary embodiment, FIG. 1 shows a packaged orthodontic assembly designated by the numeral 100. The orthodontic assembly 100 includes a container 102 having a chamber 104, and an appliance 150 received in the chamber 104. The appliance 150 is secured in the chamber 104 via support structure 120, which engages an arch wire passage in the appliance body.

The chamber 104 is partially defined by vertical sidewall 106 and a horizontal bottom wall 108. The bottom wall 108 is generally planar and defines a reference plane 109. In the depicted embodiment, the bottom wall 108 and reference plane 109 are oval-shaped, thought other shapes (e.g., circular, quadrilateral, etc.) may be suitable in other implementations. The side wall 106 is integrally connected to the bottom wall 108 and is slightly angled relative to the reference plane 109. Alternatively, the side wall 106 may be substantially orthogonal to the reference plane 109. The sidewall 106 in the depicted embodiment defines an oval in plan view, but like bottom wall 108 may define other shapes as desired. An upper edge 107 of the sidewall 106 is connected to a flange 110 that surrounds the chamber 104. The flange 110 is typically, substantially parallel with the reference plane 109.

An orthodontic appliance 150 is suspended in the chamber 104. As shown, the appliance 150 is a buccal tube: a molar appliance having a base 152 and a body 154 extending outwardly from the base 150. The body 154 includes wall sections defining a passage 156 that extends in a mesial-distal direction across the body for receipt of an archwire. The passage 156 is partially enclosed, in that it is only accessible via its opposing ends. In other embodiments, a partially enclosed passage in the appliance body may include a wall section that does not extend across the length of body or other corresponding wall sections, resulting in openings or access points in addition to the opposing ends. The base 152 has a bonding surface 159 adapted for attachment to a tooth surface and optionally an adhesive (not shown) extending across at least a portion of the bonding surface 159. It is to be understood that the container 104 could be adapted for use with other orthodontic appliances, including, for example, brackets, buttons, cleats, and sheaths. Moreover, the appliance 150 may be suitable for attachment either to the labial or lingual surface of the patient's teeth.

Figure 2:
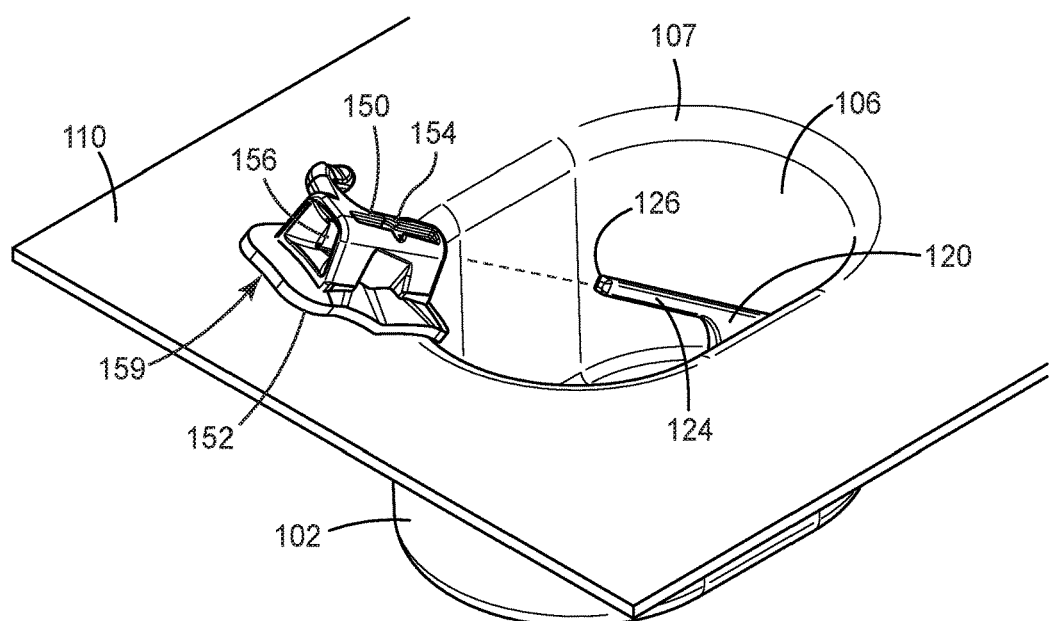
FIG. 2 is an exploded view of the assembly of FIG. 1.
Figure 3:
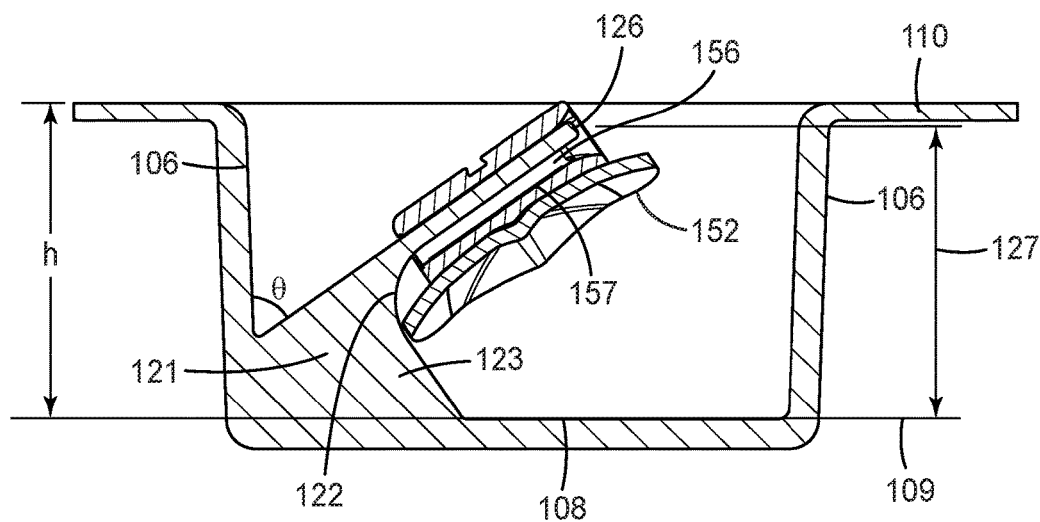
FIG. 3 is a side cross-sectional view of the packaged orthodontic assembly of FIG. 1.

As best illustrated in FIGS. 2 and 3, the appliance support structure 120 includes a support body 121 and a post 124 extending into the chamber 104 in the general direction of the upper edge 107 and flange 110. The support body 121 extends between a portion of the post 124 and the bottom wall 108 and orients the post 124 at an angle θ relative to the sidewall 106. In certain circumstances, the angle θ is selected to position the appliance adjacent the container opening. Such an orientation can render the removal of the appliance easier for a practitioner or other user. In some embodiments, the angle θ is at least 5, at least 15, at least 20, or at least 30 degrees. In some embodiments, the angle θ is at most 90, at most 75, at most 60, at most 50, or at most 45 degrees.

As can be seen in FIG. 3, the support structure 120 includes an enlarged stop 122 where the body 121 transitions to the post 124. The stop 122 can provide a limit of travel for an engaged appliance 150, preventing the appliance 150 or the adhesive (if present) from contacting the bottom wall 108, side wall 106, or support body 121. In certain implementations, the stop 122 includes a portion of body 121 having cross-sectional dimensions greater than the cross-sectional dimensions of the arch wire passage 156 on the appliance 150. The stop 122 may further include an angled fin 123 designed to assist in fixing the location of post 124 within the chamber. The fin 123 may also, in certain embodiments, contact a portion of the base 152 of the appliance 150 when the appliance 150 is received on the post 124. In other implementations, the fin 123 serves as a tactile indicator that the appliance 150 has been placed on the post 124 in the desired orientation.

The post 124 extends from the body 122 to a free end 126 positioned at a certain height 127 relative to the bottom wall 108. The height 127 is typically selected to be less than the height "h" of side wall 106, so that substantial portion of the appliance 150 remains below the flange 110. In one exemplary construction, the height 127 of the post is 0.258 inches and the height of the sidewall 106 is 0.275 inches. The length 125 of the post 124 can, as depicted in FIG. 3, be sufficient to extend through the passage 156 of the appliance, such that the end 126 is disposed outside the passage 156. In alternative implementations, the post 124 extends through a lesser portion of the passage 156.

The post 124 includes a rectangular-shaped cross-section. The cross-sectional dimensions of the post 124 can, in certain advantageous circumstances, correspond to dimensions of the arch wire passage 156. The post 124 may further include a taper along its length 125, such that at least one cross-sectional dimension at the base of the post 124 near stop 122 is greater than the corresponding dimension at the end 126. In other implementations, the cross-sectional dimensions of the post 124 are substantially constant along its length 125. The post 124 can feature other configurations, including for example, polyhedral, conical, frusto-conical, pyramidal, frusto-pyramidal, cylindrical, and combinations thereof.

As a result of the mechanical engagement between the arch wire passage 156 and the post 124, the appliance 150 is suspended in a relatively fixed position above the bottom wall 108. In this position, the appliance 150 and its associated adhesive (if present) are vertically spaced apart from the bottom wall 108 and horizontally spaced apart from side wall 106, thus avoiding substantial contact between the adhesive and the container 104. Moreover, no wall section of the passage 156 is parallel or substantially parallel to the reference plane 109, particularly wall section 157 nearest to the bottom wall 108. In the depicted embodiment, wall section 157 is a lingual wall.

In certain implementations, the post can be sufficiently soft that a portion compressively deforms upon the urging of the appliance 150 toward the support body 121. This deformation, which may be elastic, plastic, or a combination of both, can result in the post closely conforming with the interior of passage 156, resulting in a more secure engagement between appliance 150 and support 120. This can be especially useful where there is significant variation amongst the geometries of different appliances. Such variation may be due to differences in prescription (e.g., torque and angulation) base sizes, minor defects, or even manufacturing tolerances. The dimensions of the arch wire receiving passage, by contrast, are less varied and more predictable. For example, some appliance types are often offered having one of two prescribed slot dimensions: 0.18 inches and 0.22 inches. Constructing a post to generally correspond to these dimensions significantly reduces the number of different containers that must be manufactured, and reduces the impact of manufacturing tolerances elsewhere in the bracket or container. Furthermore, since the dimensions of the arch wire slot are part of the appliance prescription, close adherence to these dimensions by appliance manufacturers is paramount. By using posts 124, deformable or otherwise, designed to engage an arch wire passage instead of other appliance undercuts it is possible to afford a configuration for the container 102 that can accommodate a wide variety of appliances 150 in the chamber 104.

In other embodiments, the support has one or more features that mechanically register with slots, grooves or other recesses located on the orthodontic appliance 150. In one such example, the support includes an arm extending outward from the sidewall at an angle θ (relative to the side wall) to an outer end. The outer end includes two sections spaced from each other to present a receptacle therebetween. The appliance 150 may be received in the receptacle, such that the wall sections of the passage are non-parallel to the reference plane 109. Other aspects of such receptacle containing supports are described in U.S. Pat. No. 7,841,464 (Cinader et al.).

The container 102 can be made from any of a number of suitable materials known in the art. If an adhesive is present and is light-sensitive, the walls of the chamber 104 can be made from a suitable light-blocking material, such as a polymeric-metal laminate or metal-filled polymer composite described in U.S. Patent Publication No. 2003/0196914

(Tzou et al.). The container 102 can also be formed using any of a number of known polymer processing methods, such as extrusion, injection molding, or thermoforming. In some embodiments, the polymer composite is based on a resilient thermoplastic such as polypropylene. In presently preferred implementations of the embodiment of FIGS. 1-3, the sidewall 106, the bottom wall 108, the support 120, and the flange 110 are integrally molded or otherwise formed as a unitary component.

If present on the bonding surface 159 of the appliance 150, an orthodontic adhesive may include any of a variety of bonding compositions known in the art. In presently preferred implementations, the orthodontic adhesive is a light curable adhesive that is hardenable by exposure to actinic radiation. Suitable adhesives include, for example, TRANSBOND XT brand Light Cure Adhesive and TRANSBOND PLUS brand Color Change Adhesive, both available from 3M Unitek. As another option, the adhesive can include compressible material, as described in U.S. Patent Publication No. 2008/0096150 (Cinader) and 2009/0233252 (Cinader). Further aspects of adhesive pre-coated appliances are described in U.S. Pat. No. 5,575,645 (Jacobs, et al.), U.S. Pat. No. 6,960,079 (Brennan et al.), and U.S. Pat. No. 7,910,632 (Cinader et al.).

The container 102 can also include a cover (not shown) that is releasably connected to the flange 110 by a section of adhesive. Suitable constructions and materials for the cover and adhesive are described in the aforementioned U.S. Pat. No. 5,328,363 (Chester, et al.) and U.S. Pat. No. 5,575,645 (Jacobs, et al.), as well as U.S. Publication No. 2003/0196914 (Tzou, et al.). Alternatively, the cover may be connected to the flange 110 by a heat seal. In its closed position, the cover extends over the opening of the chamber 104 and helps protect the appliance 150 and the adhesive material (if used) from exposure to light, moisture and contaminants. The cover can include a tab that extends past the flange 110 for gripping by the practitioner when it is desired to move the cover from a closed position to an open position.

Figure 4:
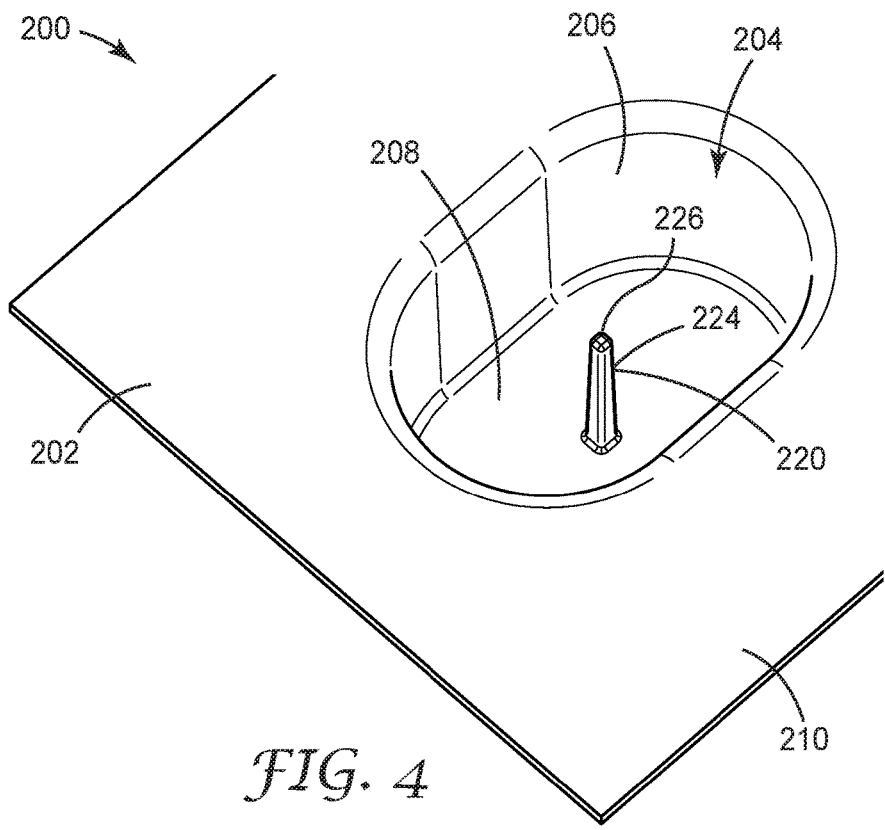
FIG. 4 is an isometric view of a container for receiving an orthodontic appliance according to another embodiment of the present disclosure.
Figure 5:
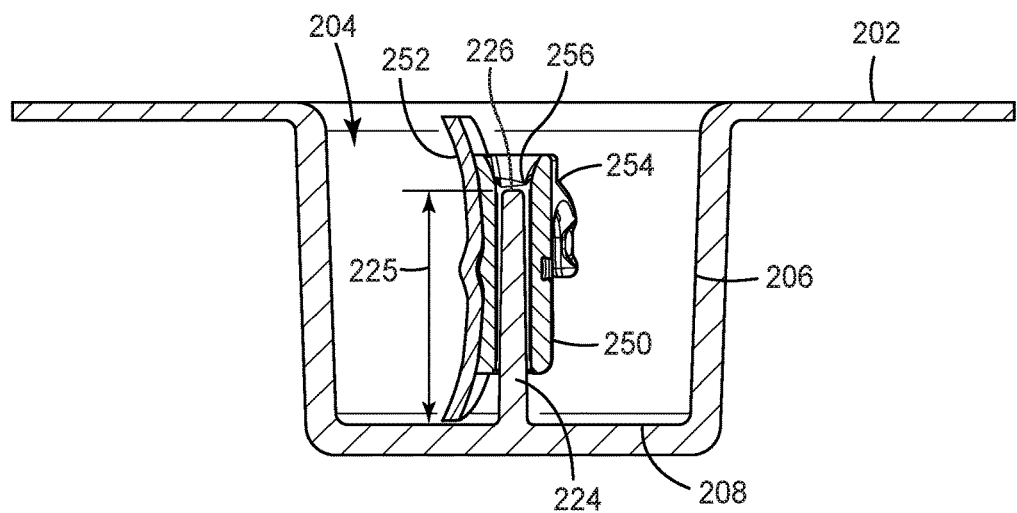
FIG. 5 is a fragmentary, cross-sectional plan view of the container of FIG. 4, including an appliance received in a chamber.

FIGS. 4 and 5 show a packaged assembly 200 according to another embodiment. The assembly 200 includes a container 202 with a chamber 204, and an appliance 250 received on a support 220. As before, the appliance 250 has a base 252, a body 254 extending outwardly from the base 252 and a partially enclosed arch wire passage 256. It is to be understood that other aspects of the assembly 200 not specifically discussed are similar to those previously described for assembly 100. The assembly 200 differs from previous embodiments in that the support 220 includes a post 224 extending into the chamber 204 from a bottom wall 208. The post 224 is oriented substantially orthogonal to the bottom wall 208 and reference plane 209. The post 254 also orients at least two wall sections of the passage 256 substantially orthogonal to the bottom wall 208.

The post 224 includes a taper along its length 225, such that at least one cross-sectional dimension at the base of the post 224 adjacent the bottom wall 208 is greater than the corresponding dimension at the end 226. The tapered profile prevents the base 252 of the appliance 205 and adhesive, if used, from contacting the bottom wall 208. Suitable post shapes in this embodiment also include without limitation frusto-conical, pyramidal and frusto-pyramidal.

Figure 6:
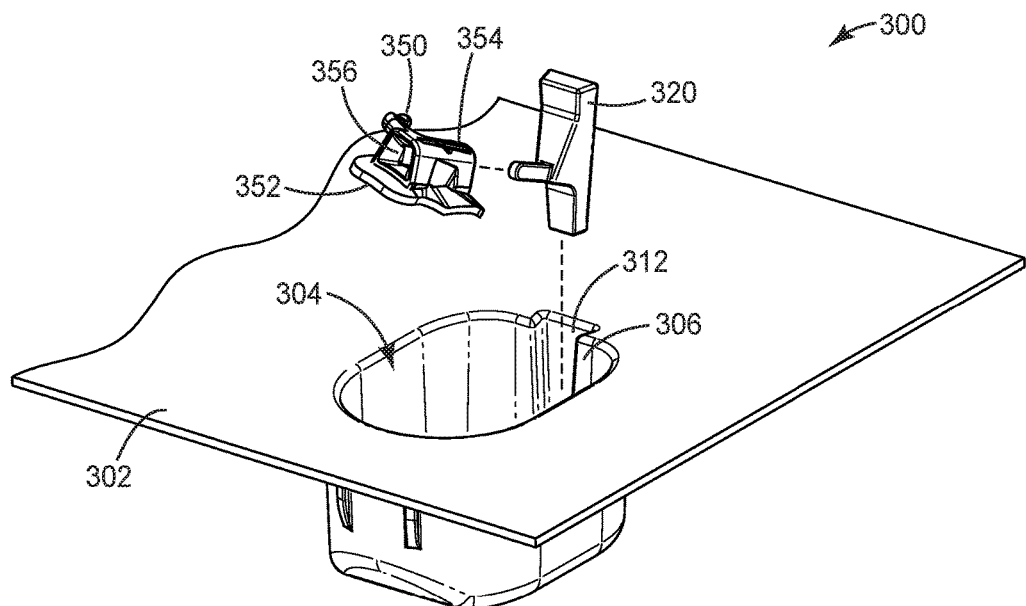
FIG. 6 is an exploded, isometric view of a packaged orthodontic assembly according to another embodiment of the present disclosure.
Figure 7:
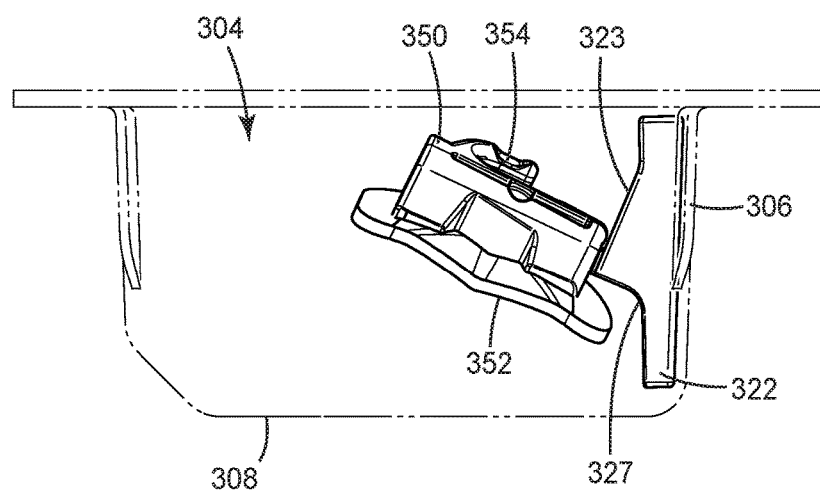
FIG. 7 is a side cross-sectional view of the packaged orthodontic assembly of FIG. 6.

FIGS. 6 and 7 show a packaged assembly 300 according to still another embodiment. The assembly 300 includes a container 302 with a chamber 304, and an appliance 350 suspended in the chamber 304 via support 320. As before, the appliance 350 has a base 352, a body 354 extending outwardly from the base 352, and a partially enclosed passage 356 extending in a mesial-distal direction across the body 354. It is to be understood that other aspects of the assembly 300 not specifically discussed are similar to those previously described for assemblies 100, 200.

In contrast to the integral support structures of the prior embodiments, support 320 includes a discrete body 322 received in the chamber 304. The sidewall 306 includes a channel 312 extending from the flange 310 to the bottom wall 308. In other embodiments, the channel 312 may extend only partially between the flange 310 and bottom wall 308. The channel 312 is dimensioned to receive the body 322 and funnel towards or otherwise position the support 320 relative to the bottom wall 308.

Figure 8:
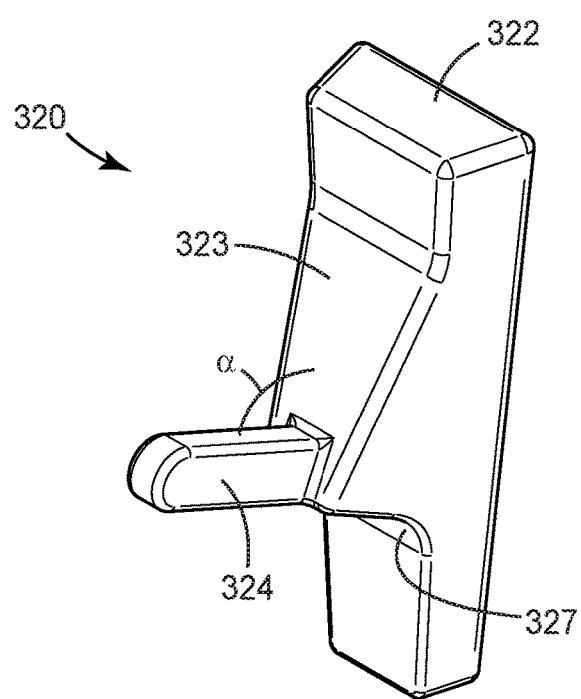
FIG. 8 is an isometric view of the appliance support structure depicted in FIGS. 6 and 7.

Turning briefly to FIG. 8, the body 322 includes a post 324, a canted wall portion 323 serving as a travel stop, and a recess 327 formed between the canted wall 323 and the body 322. The body 322 features a tapered profile to assist in insertion into the channel 312, though other profiles are possible. The post 324 extends outwardly from the canted wall 323, forming an angle $\alpha$. In certain circumstances, the angle $\alpha$ is selected to position the appliance adjacent the container 304 opening and away from bottom wall 308. Such an orientation can make the removal of the appliance easier for practitioner or other user. In some embodiments, the angle $\alpha$ is at least 5, at least 15, at least 20, or at least 30 degrees. In some embodiments, the angle $\alpha$ is at most 70, at most 65, at most 60, at most 50, or at most 45 degrees.

The support may be fixedly or releasably received in channel 312. As defined herein, supports 320 which are "fixed" to chamber are constrained such that they do not substantially move or deflect relative to the chamber 312. It is understood, however, that manufacturing tolerances may allow for one or more small gaps between the support 320 and the channel 312 and can result in a slight relative movement between these elements. In one example, the body 322 is press fit into the channel 312, which can have a shape that is complemental to at least a portion of the body 322 such that there is no substantial movement of the body 322 within the channel 312. Alternatively, the support 320 may be adhesively coupled to the channel 312.

In the embodiment depicted in FIGS. 6-7, the support 320 is releasably received in the channel 312. Use of a releasable support 320 allows for added flexibility when inserting or extracting the appliance from the chamber 304. In one alternative, the appliance 350 may be secured to the support 320 before the support body 322 is placed into channel 312. The practitioner or other user may then remove the support 320 from the channel 312 prior to disengaging the appliance 350 from the post 324. Such construction may allow for a smaller chamber volume, since the chamber 304 does not necessarily need to accept gloved fingers or other hand instrument to ensure proper removal of the appliance 350.

As can be appreciated by reference to FIG. 7, a portion of the base 352 is received in the recess 327 between body 322 and canted wall 323, allowing a greater portion of the post 324 to extend into the appliance passage 356. This configuration also allows for the canted wall 323 to abut the opening of the arch wire passage 356, offering additional security when the appliance 350 is inadvertently jostled in the chamber 304 during transit. As a partial consequence, the post 324 need not extend through the entire arch wire passage 356.

Figure 9:
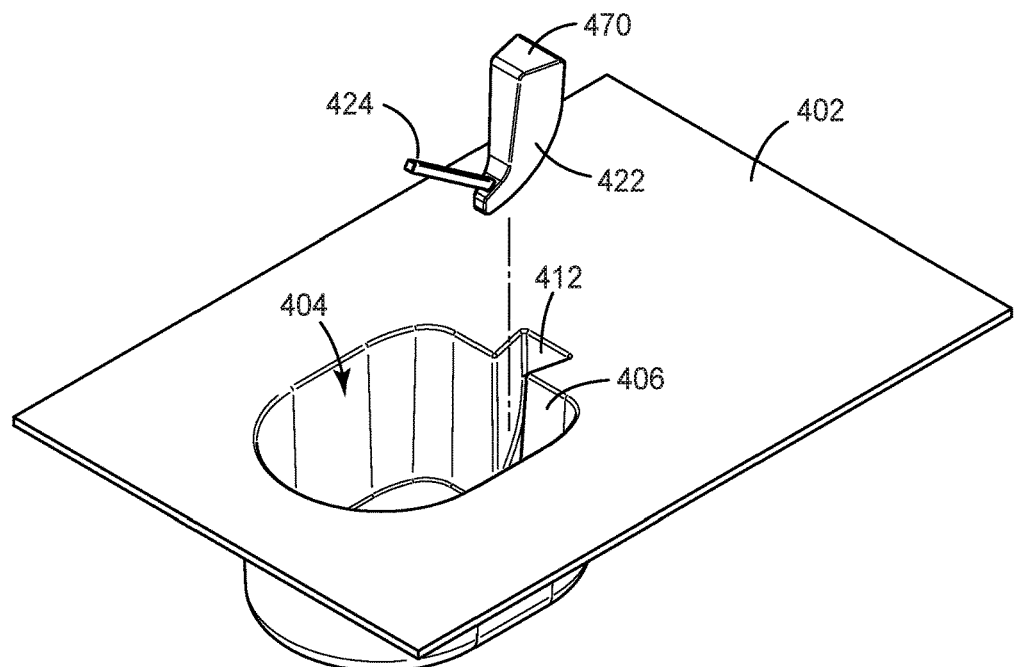
FIG. 9 is an exploded, isometric view of a package including a removable support structure according to another embodiment of the present disclosure.
Figure 10:
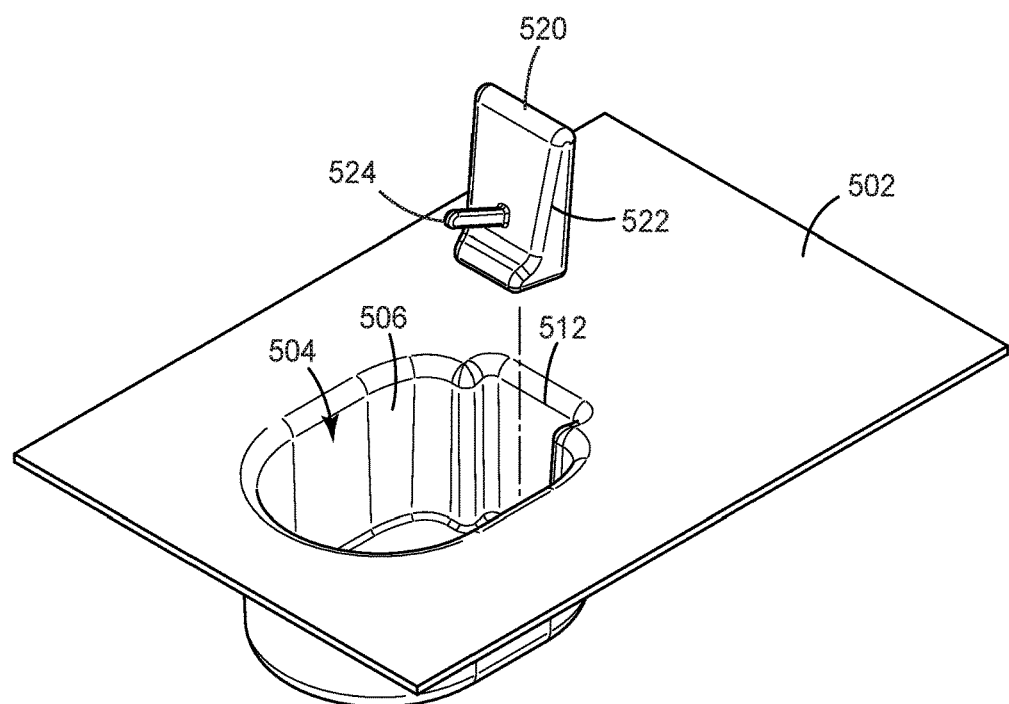
FIG. 10 is an exploded, isometric view of a package including a removable support structure according to yet another embodiment of the present disclosure.

FIGS. 9 and 10 depict alternative constructions for the discrete support and channel in packaged assemblies 400 and 500. Notably, the supports 420, 520 are constructed to position the post 424, 524, closer to the bottom wall of the chamber. Such construction may allow for larger appliances to be received in the container.

Suitable materials for the supports 320, 420, and 520 include, for example, metallic materials (such as stainless steel), ceramic materials (such as monocrystalline or polycrystalline alumina), and plastic materials (such as fiber-reinforced polycarbonate). In certain presently preferred circumstances, the support is integrally made as a unitary component by a metal injection molding or additive manufacturing process. As an alternative, however, the post may be manufactured separately and then connected directly to the canted wall by adhesive, weld, brazening, or like operation. Components of the support may be manufactured according to any number of methods known to the skilled artisan. These methods include, but are not limited to, milling, investment casting, metal injection molding, and additive manufacturing.

Figure 11:
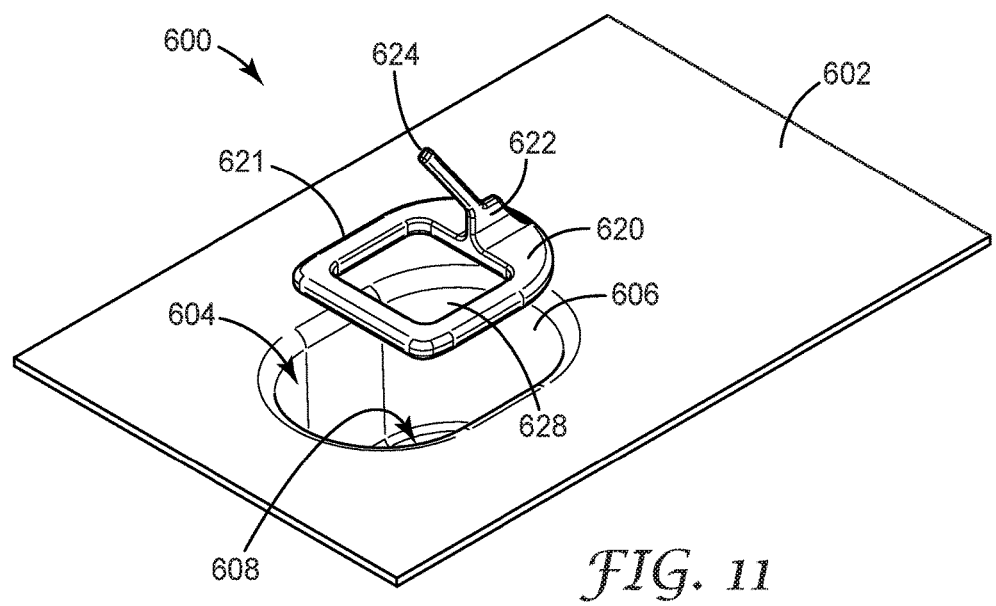
FIG. 11 is an exploded, isometric view of a package including a removable support structure according to yet another embodiment of the present disclosure.

FIG. 11 depicts a portion of a packaged assembly 600 according to still another implementation of the present disclosure. The assembly 600 includes a container 602 with a chamber 604, and a discrete support 620 received the chamber 604. The chamber 604 includes sidewalls 606 and a generally planar bottom wall 608. Instead of a channel, however, the support 620 includes a frame 621 received adjacent the bottom wall 608 in addition to post 624 and body 622. Similar to support 120, however, the post 624 is oriented at an angle relative to the bottom wall 608 once the support 620 is placed in the package. Since the post 624 is positioned at an edge region of the support 620, material in the center 628 can be omitted to enhance removability. It is to be understood that only a partial view is shown and other aspects of the assembly 600 are similar to those previously described for the above assemblies.

Figure 12:
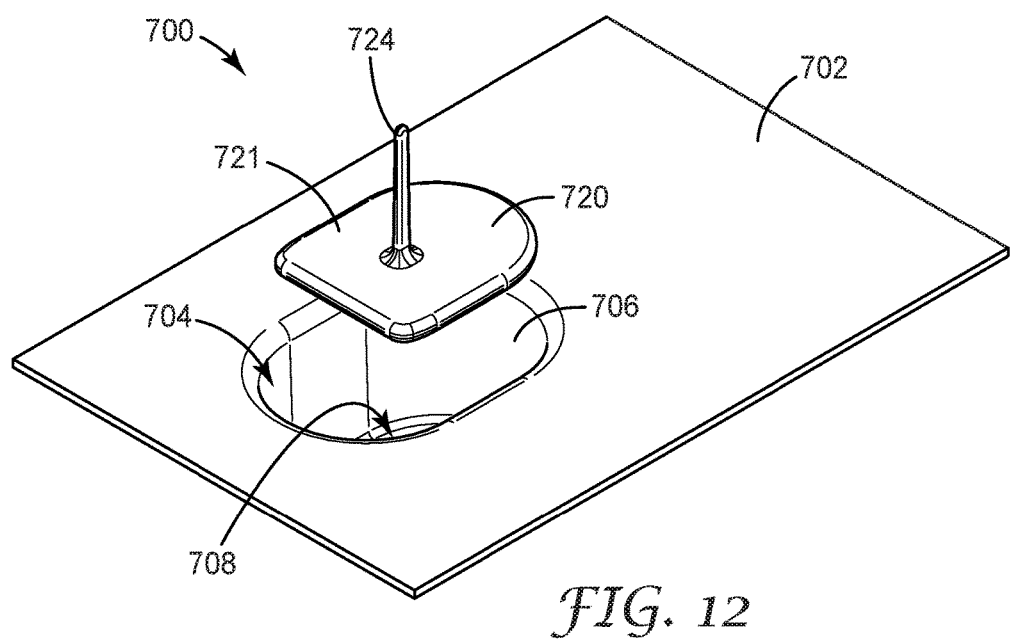
FIG. 12 is an exploded, isometric view of a package including a removable support structure according to still yet another embodiment of the present disclosure While the above-identified figures set forth several embodiments of the disclosure other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

FIG. 12 depicts a portion of a packaged assembly 700 according to yet another implementation of the present disclosure. The assembly 700 includes a container 702 with a chamber 704, and a discrete support 720 received the chamber 704. The chamber 704 includes sidewalls 706 and a generally planar bottom wall 708. Like assembly 600, the support 720 includes a frame 721 received adjacent the bottom wall 708 in addition to post 724 and body 722. More similar to support 220, however, the post 724 is oriented substantially orthogonal relative to the bottom wall 708 and the frame 721. It is to be understood that only a partial view is shown and other aspects of the assembly 700 are similar to those previously described for the above assemblies.

In an exemplary method of packaging an orthodontic assembly 100, the base of the appliance 150 in FIGS. 1-2 is optionally coated with an orthodontic adhesive. The appliance 150 is then made to slide on to the post 124 until it engages the stop 122. To seal the appliance 150 from light, moisture, and/or contaminants, the cover is then placed over both the appliance 150 and the chamber 104.

It is understood that the above methods can also apply by analogy to assemblies 200, 300, 400, 500, 600, and 700. For containers featuring removable supports (e.g., 320, 420, 520, 620, 720), the appliance may be engaged with support before or after it is placed in the chamber.

Embodiments

1. A packaged orthodontic assembly comprising: a container with a chamber, the chamber including a sidewall and a bottom wall, the bottom wall defining a reference plane; an orthodontic appliance received in the chamber, the appliance including a base and a passage having a lingual wall; a support extending into the chamber, wherein the support is engaged with the orthodontic appliance and orients the appliance such that the lingual wall is not parallel to the reference plane.
2. The assembly of embodiment 1, wherein the support includes a post having a length, wherein at least a portion of the length is received in the passage.
3. The assembly of embodiment 1, wherein the support extends into the chamber from the sidewall.
4. The assembly of embodiment 1, wherein the support extends into the chamber from the bottom wall.
5. The assembly of embodiment 3, wherein the support includes a post that extends at an oblique angle relative to the sidewall.
6. The assembly of embodiment 1, wherein the support comprises a body and a post, and wherein the post extends from a surface of the body.
7. The assembly of embodiment 6, wherein the container includes a channel adjacent the chamber, and wherein a portion of the body is releasably secured in the channel
8. The assembly of embodiment 1, wherein the support includes a frame, and wherein the frame includes a plane parallel to the reference plane.
9. The assembly of embodiment 8, wherein the support is removably received in the chamber.
10. The support of any of the previous embodiments, wherein the post comprises a rectangular cross-section.
11. The support of any of the previous embodiments, wherein the post includes a circular, ovular, or elliptical cross-section.
12. The support of embodiment 10, wherein a cross-sectional dimension varies along the length of the post.
13. The support of any of the previous embodiments, wherein the post has a frustoconical shape.
14. A packaged orthodontic assembly comprising: a container with a chamber, the chamber including a sidewall and a bottom wall; an orthodontic appliance received in the chamber, the appliance including a base and a partially enclosed passage; a support extending into the chamber, the support comprising a post having a length, wherein at least a portion of the post's length is received in the passage, thereby securing the appliance in the container.
15. The assembly of embodiment 14, wherein the post extends from the sidewall at an oblique angle.
16. The assembly of embodiment 14, wherein the post extends into the chamber from the bottom wall, wherein the post forms a substantially straight angle with the bottom wall.
17. The assembly of any of the previous embodiments, wherein the support comprises a body, and wherein the post extends from a surface of the body.
18. The assembly of embodiment 17, wherein the container includes a channel adjacent the chamber, and wherein a portion of the body is releasably secured in the channel
19. The assembly of embodiments 14-16, wherein the post is integrally formed with a sidewall or bottom wall.
20. The assembly of any of the previous embodiments, wherein the appliance further includes a hardenable dental composition extending across at least a portion of the base.
21. The assembly of embodiment 20, wherein the hardenable composition includes a compressible material.
22. The assembly of embodiment 21, wherein the hardenable composition further includes an orthodontic adhesive.
23. The assembly of any of the previous embodiments, wherein the orthodontic appliance comprises a molar appliance.

24. The assembly of embodiment 23, wherein the molar appliance is a buccal tube.

25. A packaged orthodontic assembly comprising: a container with a chamber, the chamber including a sidewall and a bottom wall; an orthodontic appliance received in the chamber, the appliance including a base and a partially enclosed passage, wherein the base includes a hardenable dental composition extending across at least a portion of the base; a support removably received in the chamber, the support comprising a post having a length, wherein at least a portion of the post's length is received in the passage, securing the appliance in the chamber.

26. The assembly of embodiment 24, wherein the support comprises a body, and wherein the post extends into the chamber from a surface of the body.

27. The assembly of embodiment 26, wherein the container includes a channel adjacent the chamber, and wherein a portion of the body is releasably secured in the channel 28. The assembly of embodiment 24, wherein the support includes a floor, and wherein the floor includes a plane parallel to the reference plane.

29. The assembly of embodiment 24, wherein the container includes a cover, and wherein the appliance is located in a position adjacent the cover when the cover is closed.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. A packaged orthodontic assembly comprising:
   a container with a chamber, the chamber including a sidewall and a bottom wall, the bottom wall defining a reference plane, wherein the sidewall comprises an upper edge connected to a flange that surrounds the chamber, and wherein the flange is substantially parallel to the reference plane;
   an orthodontic appliance received in the chamber, the appliance including a base and a passage having a lingual wall; and
   a support extending into the chamber, wherein the support comprises a support body that tapers into an elongate linear post extending along a direction from the bottom wall of the chamber toward the upper edge of the sidewall and forming an oblique angle relative to the sidewall adjacent to the support body,
   wherein at least a portion of the linear post is engaged with the passage in the orthodontic appliance and orients the appliance such that the lingual wall is not parallel to the reference plane.

2. The assembly of claim 1, wherein a cross-sectional dimension varies along the length of the post.

3. The assembly of claim 1, wherein the post comprises a free end positioned at a height below the flange that surrounds the chamber.

4. The assembly of claim 1, wherein the support extends from a frame removably receivable in the chamber, wherein the support body extends from an upper side of the frame, and wherein an underside of the frame opposite the upper side thereof is received adjacent to the bottom wall of the chamber.

5. The assembly of claim 4, wherein the frame comprises an aperture.

6. The assembly of claim 1, wherein the support comprises an enlarged stop wherein the support body transitions to the linear post, wherein the enlarged stop has a cross-sectional dimension greater than the cross-sectional dimension of the passage in the orthodontic appliance.

7. The assembly of claim 6, wherein the support body comprises an angled fin that contacts the base of the orthodontic appliance when the passage of the orthodontic appliance is received on the linear post.

8. The assembly of claim 1, wherein the linear post tapers along the length thereof.

9. The assembly of claim 1, wherein the linear post is elastically deformable, plastically deformable, or a combination thereof.

10. A packaged orthodontic assembly comprising:
    a container with a chamber including a sidewall and a bottom wall, the bottom wall defining a reference plane, wherein the sidewall comprises an upper edge connected to a flange that surrounds the chamber, and wherein the flange is substantially parallel to the reference plane;
    an orthodontic appliance received in the chamber, the appliance including a base and a partially enclosed passage; and
    a frame configured to removably mount in the chamber, wherein the frame comprises a lower side received on the bottom wall of the chamber and an upper side comprising a support for the orthodontic appliance, the support comprising a support body that extends into the chamber and tapers into an elongate linear post extending along a direction from the bottom wall of the chamber toward the upper edge of the sidewall and forming an oblique angle relative to the sidewall adjacent to the support body,
    wherein at least a portion of the linear post is engaged with the passage in the orthodontic appliance to secure the orthodontic appliance in the container.

11. The assembly of claim 10, wherein the frame comprises an aperture.

12. The assembly of claim 10, wherein the base of the orthodontic appliance includes a hardenable dental composition extending across at least a portion of the base.

13. A method for packaging an orthodontic appliance, the orthodontic appliance comprising a partially enclosed passage and a base with an adhesive layer, the method comprising:
    providing a container with a chamber including a sidewall and a bottom wall, wherein the sidewall comprises an upper edge connected to a flange that surrounds the chamber, and wherein the flange is substantially parallel to the bottom wall of the chamber;
    providing a frame configured to removably mount in the chamber, wherein the frame comprises an upper side comprising a support for the orthodontic appliance, the support comprising a support body that tapers into an elongate deformable linear post;
    mounting the orthodontic appliance on the elongate deformably linear post such that at least a portion of the elongate linear post conforms with an interior of the passage in the orthodontic appliance to removably secure the orthodontic appliance on the post; and
    inserting the frame in the chamber such that a lower side thereof is received on the bottom wall of the chamber and the elongate deformable linear post extends along a direction from the bottom wall of the chamber toward the upper edge of the sidewall and forms an oblique angle relative to the sidewall adjacent to the support body such that the base of the orthodontic appliance removably secured on the post is spaced apart from the bottom wall.

14. The method of claim 13, wherein the frame comprises an aperture.

15. The method of claim 13, further comprising applying a cover over the chamber, wherein the cover is releasably connected to the flange on the container with an adhesive.

16. The method of claim 15, wherein the cover comprises a tab that extends past the flange on the container.

* * * * *

UNITED STATES PATENT AND TRADEMARK OFFICE
CERTIFICATE OF CORRECTION

PATENT NO. : 10,307,232 B2  
APPLICATION NO. : 15/554359  
DATED : June 4, 2019  
INVENTOR(S) : Alan Conley et al.

Page 1 of 1

It is certified that error appears in the above-identified patent and that said Letters Patent is hereby corrected as shown below:

In the Specification

Column 4  
Line 17, delete "disclosure" and insert -- disclosure. --, therefor.

Column 10  
Line 19, delete "channel" and insert -- channel. --, therefor.

Column 10  
Line 53, delete "channel" and insert -- channel. --, therefor.

Column 11  
Line 18, delete "channel" and insert -- channel. --, therefor.

Signed and Sealed this  
Twenty-eighth Day of April, 2020

Andrei Iancu  
*Director of the United States Patent and Trademark Office*